United States Patent [19]

Kuhlmann et al.

[11] 4,358,600

[45] Nov. 9, 1982

[54] PROCESS FOR THE MANUFACTURE OF MALEIC ANHYDRIDE HAVING IMPROVED AGE MOLTEN COLOR

[75] Inventors: George E. Kuhlmann; Juergen K. Holzhauer, both of Naperville, Ill.

[73] Assignee: Standard Oil Company (Indiana), Chicago, Ill.

[21] Appl. No.: 268,585

[22] Filed: May 29, 1981

[51] Int. Cl.$^3$ ............................................. C07D 307/60
[52] U.S. Cl. ................................................... 549/262
[58] Field of Search ...................... 260/346.76, 346.74

[56] References Cited

U.S. PATENT DOCUMENTS 2,296,218  9/1942  Middleton ...................... 260/346.76
3,975,408  8/1976  Boyer et al. ...................... 260/346.74

Primary Examiner—Henry R. Jiles
Assistant Examiner—Bernard Dentz
Attorney, Agent, or Firm—Gunar J. Blumberg; William T. McClain; William H. Magidson

[57] ABSTRACT

A novel process for obtaining maleic anhydride having age molten and Hazen color below 125 after 20 hours at 140° C., said process comprising polymerizing at a temperature of about 53° to 90° C. in the presence of metal chloride catalyst, color bodies present in crude maleic anhydride prior to fractionating the crude maleic anhydride and distilling off the purified maleic anhydride.

8 Claims, No Drawings

PROCESS FOR THE MANUFACTURE OF MALEIC ANHYDRIDE HAVING IMPROVED AGE MOLTEN COLOR

BACKGROUND OF THE INVENTION

1. Field of the Invention

The field of this invention relates to the production of maleic anhydride from n-butane having improved aged molten color.

2. Background

Maleic anhydride is of significant commercial interest throughout the world and is extensively used in the manufacture of alkyd resins. It is also a versatile intermediate for chemical synthesis. Consequently large quantities of maleic anhydride are produced each year to satisfy these needs. The production of maleic anhydride by the catalytic oxidation of benzene and butane is well known and the principal method currently employed for the manufacture of maleic anhydride is by the air oxidation of benzene in the presence of certain heavy metal oxide catalysts. However, because of the inherent toxicity of benzene fumes, the trend has been to eliminate utilization of benzene as a feedstock and modern facilities tend to utilize butane oxidation processes to produce maleic anhydride.

Crude maleic anhydride is generally very dark in color and even though the crude maleic anhydride can be refined, the color reappears upon storage. Color is an undesirable characteristic of maleic anhydride and if present before or during processing can cause deleterious effects in resulting products such as plastics where proper color is an important feature of the material.

The prior art discloses various methods for refining crude maleic anhydride to obtain a high-grade product of low color. One such method is disclosed in U.S. Pat. No. 3,115,543 wherein color stabilizing amounts of ethylenediaminetetraacetic acid are added to a molten cyclic anhydride during the preparation process or thereafter. Alternatively, the acid is added to the final solid maleic anhydride prior to compressing into tablets or briquets. Another method is taught in U.S. Pat. No. 3,596,703 wherein small amounts of a stabilizer are incorporated into maleic anhydride. The stabilizers used are hydrochloric acid, hydrobromic acid, silver chloride, barium nitrate, alkali or alkali metal sulfates, chlorides or bromides. U.S. Pat. No. 3,975,408 provides refined maleic anhydride of improved color stability by treating the acid with elements in Group IV(b) of the periodic table and the transition elements, vanadium, chromium, manganese, mercury, silicon, phosphorus, bismuth, antimony, lead, cerium and sulfur. U.S. Pat. No. 3,939,183 discloses a method for obtaining purified maleic anhydride of good color stability by combining and contacting a metal halide and $P_2O_5$ or a perborate with the crude anhydride before final distillation of the crude anhydride. U.S. Pat. No. 2,296,218 discloses a method for treating crude maleic anhydride with oxides and hydroxides of sodium, zinc, potassium, lithium, calcium, and magnesium.

None of the foregoing references disclose or suggest the novel process for manufacturing maleic anhydride from butane with improved aged molten color involving the polymerization of the color forming compounds.

It is an object of the present invention to provide purified maleic anhydride having a Hazen color of less than 20 after two hours of heating at 140° C. and less than 125 after twenty hours of heating at 140° C. A further object of the invention is to provide a process for purifying maleic anhydride which comprises polymerizing the color bodies in crude maleic anhydride at a temperature such that maleic acid does not isomerize to fumaric acid in the presence of a metal chloride catalyst. Further objects follow.

In our novel process the color bodies are polymerized in the presence of metal chlorides prior to final fractionation. Thus in our process maleic anhydride with improved molten color is distilled off while leaving as a residue the color bodies polymerized to higher boiling compounds. The advantage of our process is that the polymerization in the presence of the metal chloride catalyst can be conducted at a temperature slightly above the melting point of maleic anhydride. The usual range being 53° to 90° C. The advantage of using this low temperature is that it prevents isomerization of maleic acid to fumaric acid. Maleic acid is usually present in crude maleic anhydride and high temperature treatment prior to fractionation leads to a two-fold yield loss as follows: First, maleic acid is lost which otherwise would mostly have been dehydrated to maleic anhydride in the fractionator and second, in a continuous process additional maleic anhydride is lost in flushing the fumaric acid out of the system. In our process it is advantageous that in addition to the low temperature a metal chloride catalyst is used to polymerize the color bodies prior to fractionation. Useful metal halides include cobaltous chloride, manganous chloride, and chlorides of antimony, bismuth, chromium, iron, mercury, nickel, phosphorus, rhodium silicon, zinc, titanium and zirconium. In our process the preferred polymerization cataltysts are cobaltous chloride and manganous chloride. The amount of the metal chloride catalyst added can vary widely from 1.0 to 0.01 percent by weight of maleic anhydride down to ten parts per million based on the maleic anhydride.

One of the important specifications for the purified maleic anhydride is color stability. The color of maleic anhydride is commonly measured by so-called APHA color standards using standard platinum/cobalt solutions prepared in accordance with ASTMD-22 80-66 procedure. This color scale was developed by the American Public Health Association and it is also known as the Hazen Platinum Cobalt Scale. A description may be found on Page 2048 of the fifth edition of *Standard Method of Chemical Analysis* by Wilford W. Scott.

Typical specifications on product maleic anhydride call for an APHA or Hazen color of 20 or lower for molten anhydride and a color of 40 or less after two hours heating at 140° C. Good commercial maleic anhydride has a Hazen color below 125 after twenty hours at 140° C. The present invention provides maleic anhydride of good color stability having a Hazen color of less than 25 after two hours heating at 140° C. and less than 125 after twenty hours heating. According to the present invention an improvement is made in a process for obtaining purified maleic anhydride from crude anhydride by steps comprising polymerizing the color bodies in the crude maleic anhydride at a temperature of about 53° to 90° C. in the presence of a polymerization catalyst, distilling the crude maleic anhydride and withdrawing a purified anhydride overhead as a distilled product. The above improvement results in obtaining purified maleic anhydride of high color stability. We have found that the present invention is advantageously applied to crude maleic anhydride produced by oxidation of normal butane using a catalyst comprising vanadium and phosphorus oxides to which a metal promoter has been added. Such a catalyst is described in commonly assigned U.S. Pat. No. 3,862,146 granted Jan. 21, 1975 and also in U.S. Pats. Nos. 4,147,661 and 4,151,116. All three of these U.S. patents are incorporated herein by reference. Thus, in accordance with a preferred embodiment of the present invention a process is provided for obtaining purified maleic anhydride from crude maleic anhydride produced by steps comprising oxidizing butane over a particular solid catalyst comprising vanadium, phosphorus oxide and a metal promoter to obtain a gaseous effluent containing maleic anhydride, combining and contacting 0.001 to 1.0 weight percent of metal chloride with the crude maleic anhydride to polymerize the color body forming compounds. This polymerization is conducted at a temperature of about 53° to 90° C. for a period of about 2 to 48 hours and distilling the mixture to obtain a purified overhead maleic anhydride fraction.

The following examples illustrate the preferred embodiment of this invention. It will be understood that these examples are for illustration purposes only and do not purport to be wholly definitive with respect to the conditions or scope of this invention.

EXAMPLE 1

Crude maleic anhydride prior to fractionation was treated with one thousand parts per million of either cobaltous chloride or manganous chloride for a period of about sixteen hours at a temperature of 150° F. The samples then were compared with the crude maleic anhydride which was not treated with the metal chlorides. The results of the batch fractionations of crude maleic anhydride are shown in Table 1 hereinbelow.

TABLE I

| Batch Fractionations of Crude MAN | | | |
|---|---|---|---|
| | Un-treated | 1000 ppm $CoCl_2$* | 1000 ppm $MnCl_2$* |
| Sample Treatment | | 150° F. 16 hrs | 150° F. 16 hrs |
| Initial Molten Color | | | |
| (APHA), Cut #1 | 10–15 | 5–10 | 5–10 |
| 2 | 5–10 | 5 | 5 |
| 3 | 5–10 | 0–5 | 0–5 |
| 4 | 5–10 | 0–5 | 0–5 |
| 5 | 5–10 | 5–10 | 0–5 |
| 2-hr Aged Molten | | | |
| Color, Cut #1 | 150 | 50–60 | 80–90 |
| 2 | 70–80 | 5–10 | 15–20 |
| 3 | 50–60 | 5–10 | 5–10 |
| 4 | 30–35 | 5–10 | 5–10 |
| 5 | 20–25 | 5–10 | 5–10 |
| 20-hr Aged Molten | | | |
| Color, Cut #1 | — | 800 | 1500 |
| 2 | — | 30–35 | 1500 |
| 3 | — | 30–35 | 100 |
| 4 | — | 70–80 | 15–20 |
| 5 | — | 80–90 | 50–60 |

*Added as $CoCl_2.6H_2O$ and $MnCl_2.4H_2O$, calculated on an anhydrous basis.

EXAMPLE 2

Samples of crude maleic anhydride from commercial plants and pilot prior to final fractionation were obtained and treated with cobaltous chloride. The results of this experiment are shown in Table II.

TABLE II

| Source of Crude Maleic Anhydride | Treatment Prior to Fractionation | Batch Fractionations 2-hr Aged Molten Color (Cut No.) | | | | |
|---|---|---|---|---|---|---|
| | | 1 | 2 | 3 | 4 | 5 |
| Pilot Plant | Untreated | 125–150 | 60–70 | 20–25 | 20–25 | 20–25 |
| Pilot Plant | 100 ppm $CoCl_2$/ 150° F./ 16 hrs | 125–150 | 35–40 | 30–35 | 20–25 | 10–15 |
| Pilot Plant | 300 ppm $CoCl_2$/ 150° F./ 16 hrs | 100–125 | 30–35 | 25–30 | 20–25 | 10–15 |
| Pilot Plant | 1000 ppm $CoCl_2$/ 150° F./ 16 hrs | 100–125 | 30–35 | 20–25 | 5–10 | 5–10 |
| Commercial Plant | Untreated | 100–125 | 15–20 | 60–70* | 10–15 | 10–15 |
| Commercial Plant | 300 ppm $CoCl_2$/ 150° F./ 16 hrs | 45–50 | 10–15 | 30–35* | 10–15 | 5–10 |
| Commercial Plant | 1000 ppm $CoCl_2$/ 150° F./ 16 hrs | 30–35 | 20 | 20–25* | 5–10 | 10 |

*Sample stirred in soft brown glass bottle for 30 minutes at 150° F. prior to aging.

We claim:

1. A process for obtaining maleic anydride from butane having age molten Hazen color below 125 after 20 hours at 140° C., said process comprising polymerizing at a temperature of about 53° to 90° C. in the presence of at least 10 parts per million parts of maleic anhydride one of the following cobaltous chloride, manganese chloride, antimony chloride, bismuth chloride, chromium chloride, mercury chloride, nickel chloride, phosphorus chloride, rhodium chloride, silicon chloride, titanium chloride, and zirconium chloride color bodies present in crude maleic anhydride prior to fractionating the crude maleic anhydride and distilling off the purified maleic anhydride.

2. The process of claim 1 wherein the polymerization temperature is about 53° to 75° C.

3. A process for obtaining maleic anhydride from butane having age molten Hazen color below 125 after 20 hours at 140° C., said process comprising polymerizing at a temperature of 53° to 90° C. in the presence of cobaltous chloride catalyst color bodies present in the crude maleic anhydride derived from butane prior to fractionizing the crude maleic anhydride and distilling off the purified maleic anhydride.

4. The process of claim 3 wherein the polymerization temperature is about 53° to 75° C.

5. The process of claim 3 wherein the catalyst added is about 0.001 to 1.0 weight percent of the maleic anhydride.

6. A process for obtaining maleic anhydride from butane having age molten Hazen color below 125 after 20 hours at 140° C., said process comprising polymerizing at a temperature of 53° to 90° C. in the presence of manganous chloride catalyst color bodies present in crude maleic anhydride prior to fractionating the crude maleic anhydride and distilling off the purified maleic anhydride.

7. The process of claim 6 wherein the polymerization temperature is about 53° to 75° C.

8. The process of claim 6 wherein the catalyst added is about 0.001 to 1.0 weight percent of the maleic anhydride.

* * * * *

UNITED STATES PATENT OFFICE
CERTIFICATE OF CORRECTION

Patent No. 4,358,600  Dated November 9, 1982

Inventor(s) George E. Kuhlmann, Juergen K. Holzhauer

It is certified that error appears in the above-identified patent and that said Letters Patent are hereby corrected as shown below:

| Patent Column | Line | | |
|---|---|---|---|
| 2 | 32 | "rhodium silicon" should read | --rhodium, silicon-- |
| 3 | 66 | "pilot prior" should read | --pilot plants prior-- |
| 4 | 49 | "fractionizing" should read | --fractionating-- |

Signed and Sealed this

Thirteenth Day of December 1983

[SEAL]

Attest:

GERALD J. MOSSINGHOFF

Attesting Officer  Commissioner of Patents and Trademarks